United States Patent [19]

Kirkovits et al.

[11] Patent Number: 5,081,025
[45] Date of Patent: Jan. 14, 1992

[54] PROCESS FOR THE FERMENTATIVE PRODUCTION OF CITRIC ACID FROM CARBOHYDRATES

[75] Inventors: August Kirkovits, Stronsdorf; Helga Edlauer, Laa/Thaya, both of Austria

[73] Assignee: Jungbunzlauer Aktiengesellschaft, Wein, Austria

[21] Appl. No.: 592,215

[22] Filed: Oct. 3, 1990

[30] Foreign Application Priority Data

Oct. 25, 1989 [AT] Austria ................... 2461/89

[51] Int. Cl.$^5$ .................. C12R 1/685; C12P 7/48
[52] U.S. Cl. ..................... 435/144; 435/917
[58] Field of Search .................. 435/144, 917

[56] References Cited

U.S. PATENT DOCUMENTS

| | | |
|---|---|---|
| 2,492,667 | 12/1949 | Snell et al. |
| 2,492,673 | 12/1949 | Woodward et al. |
| 2,970,084 | 1/1961 | Schweiger |
| 3,326,774 | 6/1967 | Gold et al. ............ 435/144 |
| 3,936,352 | 2/1976 | Kabil ..................... 435/144 |
| 3,940,315 | 2/1976 | Hustede et al. ........ 435/144 |
| 3,941,656 | 3/1976 | Hustede et al. ........ 435/144 |

FOREIGN PATENT DOCUMENTS

| | | |
|---|---|---|
| 295448 | 1/1972 | Austria . |
| 296194 | 2/1972 | Austria . |
| 307346 | 5/1973 | Austria . |
| 526987 | 6/1956 | Canada ............... 435/144 |
| 696535 | 10/1964 | Canada ............... 435/144 |
| 342191 | 12/1959 | Switzerland . |

Primary Examiner—Herbert J. Lilling
Attorney, Agent, or Firm—Paul & Paul

[57] ABSTRACT

Proposed is a process for the fermentative production of citric acid from carbohydrates by means of a microorganism of the species *Aspergillus niger* in a substrate containing zinc ions and hexacyanoferrate ions wherein carbohydrates not prepurified are employed and the Zn content of the substrate is adjusted to 30 to 250 ppm and the hexacyanoferrate content of the substrate is adjusted to 100 to 500 ppm.

14 Claims, No Drawings

PROCESS FOR THE FERMENTATIVE PRODUCTION OF CITRIC ACID FROM CARBOHYDRATES

The invention relates to a process for the fermentative production of citric acid from carbohydrates by means of a microorganism of the species *Aspergillus niger* in a substrate containing zinc and hexacyanoferrate.

In the submersed fermentation of citric acid with use of *Aspergillus niger* from comparatively impure carbohydrate material, the detrimental influence of iron ions in the substrate has long been known.

While a content of 2.0 ppm of Fe in the substrate is amply tolerable when using carbohydrates of a high degree of purity, 0.2 ppm of Fe may already be excessive with comparatively impure carbohydrates and cause the formation of large amounts of non-acid-forming *Aspergilus niger* mycelium, while citric acid formation drops drastically. This fact is attributed to the presence of socalled "iron potentiators", such as amino acids, in the substrate which originate from the impure carbohydrates and multiply the negative effect of the iron by the formation of the non-acid-forming mycelium.

For this reason, iron antagonists were sought for processes employing comparatively impure carbohydrates and U.S. Pat. No. 2,970,084 described the use of up to 500 ppm of Cu in the substrate in order to eliminate the influence of the iron potentiators. This effective procedure, however, is accompanied by a most undesirable secondary phenomenon in the form of an accumulation of large amounts of highly toxic Cu-salts in the sewage sludge.

U.S. Pat. No. 2,492,673 describes another Fe antagonist, namely zinc. According to this publication, the citric acid fermentation of invert molasses with *Aspergillus niger* is carried out by decationizing the invert molasses with a cation exchanger (H-form) so as to reduce the Fe content to about 2 to 4 ppm and then adding 10 to 30 parts by weight of Zn per part by weight of Fe, the total zinc content not to exceed 150 ppm. But Zn-salts, although better tolerable than Cu, are not a particularly desirable component of sewage sludges, either.

CH-PS 342,191 compares Cu and Zn as Fe antagonists and states that when using comparatively impure carbohydrates, especially those which are not decationized, the employment of Zn is detrimental as compared to the use of Cu. On principle, Cu is preferred over Zn when using sugar.

The invention is based on a substrate containing Zn ions as well as hexacyanoferrate ions.

Hexacyanoferrates, for instance $K_4|Fe(CN)_6|.3H_2O$, are known mycelium growth inhibitors in the fermentative production of citric acid by means of *Aspergillus niger* and are preferably added in amounts of $\leq 10$ ppm, see AT-PS 295,448 and 296,194.

AT-PS 307,346 discloses a citric acid fermentation medium containing 1.5 ppm $ZnSO_4.7H_2O$ and $\leq 10$ ppm $K_4|Fe(CN)_6|$.

These Austrian patent specifications relating to the joint use of hexacyanoferrates and Zn ions describe the employment of at least partially (decationized) pre-purified sugar solutions in which zinc acts as the growth promoter while hexacyanoferrate influences the development of mycelium as an inhibitor.

It was now surprisingly found that carbohydrate solutions which were not pretreated, i.e. those not clarified by precipitation and without ion exchanger treatment, may conveniently be processed in a substrate containing hexacyanoferrate and Zn ions if this substrate contains 30 to 250 ppm of Zn and 100 to 500 ppm of hexacyanoferrate.

This affords most favorable yields of citric acid at troublefree course of process without the necessity of monitoring the process and without chemical and/or physical control measures (e.g. without current pH regulation). Moreover, a tolerable sewage sludge is obtained even at high salt concentrations in the substrate.

Zn and hexacyanoferrate are each preferably used in amounts of about 100 ppm.

In particular, at least so many Zn ions and hexacyanoferrate ions are added to the substrate that a precipitation product forms which is then not separated.

Mono and/or disaccharides, in particular glucose, are preferably used as the untreated carbohydrates; the use of other carbohydrate sources, such as those of cane or beet molasses, is also possible.

One of the characterizing features of the process according to the invention resides in the fact that all the manipulations required for the economical production of citric acid can be carried out at the start of fermentation. Constant monitoring of fermentation and intervention on the basis of particular chemical or physical parameters such as pH value and the formation of mycelium are not necessary.

The citric acid thus obtained many be isolated and processed according to one of the conventional known processes.

The invention is explained in detail by means of the following examples which were carried out with the microorganism *Aspergillus niger* 6074 which was deposited according to the Budapest Convention in the Deutsche Sammlung von Mikroorganismen (German Collection of Microorganisms) Mascheroder Weg 1B, D-3300 Braunschweig on Aug. 16, 1989 and received the accession number DSM 5484 and is characterized by the following features:

the multi-septated, polynuclear mycelium is provided with a large number of conidia supports;
a typical formation of small heads due to bulbously enlarged hyphae on whose surfaces there are sterigma with black to brownish-black conidia arranged in the form of pearl strings is observable;
morphology of colonies:
  initially white to yellowish, of cottonlike consistency; after several days, black to brownish-black due to the formation of conidia;
  diameter of hyphae: 2–8 $\mu$m
  length of conidia supports: up to 6 $\mu$m
  diameter of conidia: 4–6 $\mu$m with rugged surface At suitable cultivation conditions, the microorganism *Aspergillus niger* DSM 5484 shows a surprisingly high spore weight of $1-3 \cdot 10^{10}$ of individual spores/g which with other representatives of this species ranges in the order of magnitude of $8-11 \cdot 10^{10}$ of individual spores/g.

This feature can be explained by the conidia diameter which amounts to 3.7 to 4.7 mm for strains usually used for citric acid production. It should be emphasized that weight and diameter of spores are preferably obtained by cultivation on media whose carbohydrate source consists of pure raw materials, such as e.g. glucose or sucrose, and is not obtained by the addition of complex growth media such as molasses.

In contrast to the organism *Aspergillus niger* ATCC 1015 described in U.S. Pat. No. 2,492,667, the use of the strain DSM 5484 in the process according to the invention does not depend on the adherence to a transfer cycle of e.g. 5 to 7 days, but can instead be effected at any given time interval.

The cultivation of spores according to the process of the invention is preferably also to be carried out on media whose carbohydrate source consists of pure raw materials such as e.g. glucose or saccharose.

EXAMPLES 1 to 3

Spore of the fungus *Aspergillus niger* in a concentration of $10^9$ spores per liter of culture liquid, which corresponds to an amount of 10 to 15 g of spores per $m^3$, were added to a nutrient solution designated as medium 1. The incubation of the broth thus inoculated was carried out at conditions generally known and described for citric acid production, such as aeration and temperature control.

| Medium 1: | |
|---|---|
| Dextrose | 150 g |
| $(NH_4)_2SO_4$ | 1.5 g |
| $MgSO_4$ | 0.6 g |
| $KH_2PO_4$ | 0.12 g | per liter of tap water

In Example 1, neither zinc nor hexacyanoferrate were added, in Example 2, 100 ppm of $Zn^{2+}$ in the form of $ZnSO_4.7H_2O$ were added, in Example 3, 100 ppm of potassium hexacyanoferrate II were added.

The results of these tests are summarized in Table 1, expressed as percent yield of citric acid on the basis of the glucose employed:

TABLE 1

| | Yield of Citric Acid | |
|---|---|---|
| | $[K_4Fe(CN)_6]$ [ppm] | |
| $Zn^{2+}$ [ppm] | 0 | 100 |
| 0 | 1% | 18% |
| 100 | 14% | |

As evident from the Examples, an economical citric acid production without or with only one of the two additives zinc and hexacyanoferrate is not possible at the selected conditions.

EXAMPLES 4 to 16

As explained in Examples 1 to 3, zinc and hexacyanoferrate were added to the nutrient solution medium 1 in the following concentrations:

| | $Zn^{2+}$ |ppm| | $|K_4Fe(CN)_6|$ |ppm| |
|---|---|---|
| Example 4 | 30 | 100 |
| Example 5 | 50 | 100 |
| Example 6 | 50 | 150 |
| Example 7 | 100 | 100 |
| Example 8 | 100 | 150 |
| Example 9 | 100 | 200 |
| Example 10 | 150 | 100 |
| Example 11 | 150 | 150 |
| Example 12 | 150 | 300 |
| Example 13 | 200 | 100 |
| Example 14 | 200 | 400 |
| Example 15 | 250 | 100 |

-continued

| | $Zn^{2+}$ |ppm| | $|K_4Fe(CN)_6|$ |ppm| |
|---|---|---|
| Example 16 | 250 | 500 |

The fermentation was carried out at the same conditions as in the preceding Examples. The following citric acid yields were obtained:

| $Zn^{2+}$ [ppm] | $[K_4Fe(CN)_6]$ [ppm] | | | | | |
|---|---|---|---|---|---|---|
| | 100 | 50 | 200 | 300 | 400 | 500 |
| 30 | 69% | | | | | |
| 50 | 82% | 79% | | | | |
| 100 | 86% | 77% | 72% | | | |
| 150 | 79% | 71% | | 75% | | |
| 200 | 63% | | | | 63% | |
| 250 | 57% | | | | | 65% |

It is evident that economically very interesting yields are obtainable on addition of 100 ppm of $Zn^{2+}$ and 100 ppm of $|K_4Fe(CN)_6|$.

The influence of the resulting precipitation is demonstrated by means of the following two Examples:

EXAMPLES 17 AND 18

In Example 17, 50 ppm of $Zn^{2+}$ and 100 ppm of potassium hexacyanoferrate II were added to medium 1 in accordance with Example 5, in Example 18,100 ppm of $Zn^{2+}$ and 100 ppm of potassium hexacyanoferrate II were added in accordance with Example 7. In contrast to Examples 5 and 7, however, the forming precipitate was removed by means of centrifuge and the remaining blank solution was inoculated with spores in the manner previously described and subjected to the fermentation process.

Results

Example 17:46 percent yield of citric acid;
Example 18:57 percent yield of citric acid.

In comparison to the results of Examples 5 and 7 in which the suspended matter was not removed and in which the yields amounted to 82 and 86 percent, there cannot be any doubt as to the importance of the precipitation for the formation of product in the system described.

The following Example 19 describes in detail a process in which the cultivation of the inoculation material was effected in a fermenter other than the production fermenter due to particular technical conditions.

EXAMPLE 19

The nutrient salts enumerated in the preceding Examples dissolved in tap water were sterilized at a pH value of 3.0 for 30 minutes at 121° C., after cooling, 100 ppm each of $Zn^{2+}$ in the form of $ZnSO_4.7H_2O$ and 100 ppm of $K_4|Fe(CN)_6|$ were added and inoculated with spores corresponding to a concentration of $10^9$ spores per liter.

The culture conditions were selected as temperature control to 30° C., pH adjustment to 3.0 by means of ammonia and aeration of 2 vvm at a rotation speed of the disk agitator of 200 rpm so that enough inoculation material was formed after 20 to 30 hours to inoculate a production fermenter. The amount of inoculum selected for the test described was 3 percent.

The nutrient medium of the production fermenter was prepared as described above, the temperature was kept constant and aeration and agitation were adjusted according to the viscosity of the medium.

In this test, a yield of 70 percent of citric acid was obtained based on the entire amount of carbohxydrates employed.

We claim:

1. A process for the fementative production of citric acid from carbohydrates by means of a microorganism of the species *Aspergillus niger* in a substrate containing zinc ions and hexacyanoferrate ions, the improvement comprising that carbohydrates not prepurified are used and the Zn content of the substrate is adjusted to 30 to 250 ppm and the hexacyanoferrate content of the substrate is adjusted to 100 to 500 ppm.

2. The process according to claim 1, wherein the Zn content and the hexacyanoferrate content are each adjusted to about 100 ppm.

3. The process according to claim 1 or 2, wherein at least enough Zn ions and hexacyanoferrate ions are added to the substrate to cause the formation of a precipitation product.

4. The process according to claim 1 or 2, wherein the carbohydrates employed are mono and/or disaccharides.

5. The process according to claim 1 or 2, wherein the *Aspergillus niger* strain 6074 (DSM No. 5484 of Aug. 16, 1989) is used.

6. The process according to claim 1 or 2, wherein the fermentation is carried out submersively.

7. The process according to claim 4, wherein the carbohydrate employed is glucose.

8. The process according to claim 3, wherein the carbohydrates employed are mono and/or disaccharides.

9. The process according to claim 3, wherein the *Aspergillus niger* strain 6074 (DSM No. 5484 of Aug. 16, 1989) is used.

10. The process according to claim 4, wherein the *Aspergillus niger* strain 6074 (DSM No. 5485 of Aug. 16, 1989) is used.

11. The process according to claim 3, wherein the fermentation is carried out submersively.

12. The process according to claim 4, wherein the fermentation is carried out submersively.

13. The process according to claim 5, wherein the fermentation is carried out submersively.

14. The process according to claim 8, wherein the carbohydrate employed is glucose.

* * * * *